United States Patent
Pavcnik et al.

(10) Patent No.: US 6,508,833 B2
(45) Date of Patent: Jan. 21, 2003

(54) MULTIPLE-SIDED INTRALUMINAL MEDICAL DEVICE

(75) Inventors: Dusan Pavcnik, Portland, OR (US); Frederick S. Keller, Portland, OR (US); Josef Rosch, Portland, OR (US); Thomas A. Osborne, Bloomington, IN (US)

(73) Assignee: Cook Incorporated, Bloomington, IN (US)

(*) Notice: Subject to any disclaimer, the term of this patent is extended or adjusted under 35 U.S.C. 154(b) by 0 days.

(21) Appl. No.: 09/804,128

(22) Filed: Mar. 12, 2001

(65) Prior Publication Data

US 2001/0011187 A1 Aug. 2, 2001

Related U.S. Application Data

(63) Continuation of application No. 09/324,382, filed on Jun. 2, 1999, now Pat. No. 6,200,336
(60) Provisional application No. 60/087,661, filed on Jun. 28, 1998.

(51) Int. Cl.[7] .................................................. A61F 2/06
(52) U.S. Cl. .................... 623/1.15; 623/1.21; 623/1.24; 623/2.13; 623/2.14; 623/2.17; 623/2.18
(58) Field of Search ................................ 623/1.15, 1.16, 623/2.13, 2.14, 2.17, 2.18, 1.21, 1.24, 1.27, 1.13, 1.14, 1.47; 606/198; 604/104

(56) References Cited

U.S. PATENT DOCUMENTS

| | | | |
|---|---|---|---|
| 4,218,783 A | * | 8/1980 | Reul et al. .................... 3/1.5 |
| 4,580,568 A | | 4/1986 | Gianturco |
| 4,994,077 A | | 2/1991 | Dobben |
| 5,035,706 A | | 7/1991 | Gianturco et al. |

(List continued on next page.)

FOREIGN PATENT DOCUMENTS

| | | |
|---|---|---|
| EP | 0221570 | 5/1987 |
| EP | 0480667 | 4/1992 |
| EP | 0667133 | 8/1995 |
| EP | 0691108 | 1/1996 |
| EP | 0712614 | 5/1996 |
| EP | 0808614 | 11/1997 |
| EP | 0818184 | 1/1998 |
| EP | 0850607 | 7/1998 |
| EP | 0856300 | 8/1998 |
| EP | 0920842 | 9/1999 |
| JP | 9505788 | 3/1995 |
| WO | 9313712 | 7/1993 |
| WO | 9529646 | 11/1995 |
| WO | 9915224 | 4/1999 |
| WO | 9962431 | 12/1999 |

OTHER PUBLICATIONS

Flow Through A Venous Valve And Its Implication For Thrombus Formation; Takeshi Karino and Mineo Motomiya; Thrombosis Research 36; pp. 245–257; 1984.

(List continued on next page.)

Primary Examiner—Corrine McDermott
Assistant Examiner—Cheryl Miller
(74) Attorney, Agent, or Firm—Charles W. Agnew

(57) ABSTRACT

A multiple-sided medical device comprises a closed frame of a single piece of wire or other resilient material and having a series of bends and interconnecting sides. The device has both a flat configuration and a second, folded configuration that comprises a self-expanding stent. The stent is pushed from a delivery catheter into the lumen of a duct or vessel. One or more barbs are attached to the frame of the device for anchoring or to connect additional frames. A covering of fabric or other flexible material such as DACRON, PTFE, or collagen, is sutured or attached to the frame to form an occlusion device, a stent graft, or an artificial valve such as for correcting incompetent veins in the lower legs and feet. A partial, triangular-shaped covering over the lumen of the device allows the valve to open with normal blood flow and close to retrograde flow.

21 Claims, 5 Drawing Sheets

U.S. PATENT DOCUMENTS

| | | | |
|---|---|---|---|
| 5,104,399 A | * | 4/1992 | Lazarus ............ 623/1 |
| 5,108,420 A | | 4/1992 | Marks |
| 5,116,564 A | | 5/1992 | Jansen et al. |
| 5,123,919 A | | 6/1992 | Sauter et al. |
| 5,147,389 A | | 9/1992 | Lane |
| 5,171,259 A | | 12/1992 | Inoue |
| 5,334,217 A | | 8/1994 | Das |
| 5,335,341 A | | 8/1994 | Chana |
| 5,358,518 A | | 10/1994 | Camilli |
| 5,451,235 A | | 9/1995 | Lock et al. |
| 5,500,014 A | | 3/1996 | Quijano et al. |
| 5,607,465 A | | 3/1997 | Camilli |
| 5,630,829 A | | 5/1997 | Lauterjung |
| 5,643,312 A | * | 7/1997 | Fischell et al. ............ 606/198 |
| 5,643,317 A | | 7/1997 | Pavcnik et al. |
| 5,709,707 A | | 1/1998 | Lock et al. |
| 5,733,325 A | | 3/1998 | Robinson et al. |
| 5,746,766 A | | 5/1998 | Edoga |
| 5,810,847 A | | 9/1998 | Laufer et al. |
| 5,840,081 A | * | 11/1998 | Andersen et al. ............ 623/2 |
| 5,855,597 A | * | 1/1999 | Jayaraman ............ 623/1 |
| 5,855,601 A | | 1/1999 | Bessler et al. |
| 5,861,003 A | | 1/1999 | Latson et al. |
| 5,879,382 A | * | 3/1999 | Boneau ............ 623/1 |
| 5,922,020 A | * | 7/1999 | Klein et al. ............ 623/1 |
| 5,957,949 A | | 9/1999 | Leonhardt et al. |
| 6,027,525 A | | 2/2000 | Suh et al. |
| 6,077,281 A | | 6/2000 | Das |
| 6,126,686 A | | 10/2000 | Badylak et al. |
| 6,183,495 B1 | * | 2/2001 | Lenker et al. ............ 606/198 |
| 6,245,102 B1 | | 6/2001 | Jayaraman |
| 6,280,467 B1 | * | 8/2001 | Leonhardt ............ 623/1.16 |
| 6,327,772 B1 | * | 12/2001 | Zadno-Azizi et al. ......... 29/557 |
| 6,334,872 B1 | * | 1/2002 | Termin et al. ............ 623/1.38 |

OTHER PUBLICATIONS

*Radiology* vol. 189(P) Suppl., Nov. 1993, "Percutaneously Introduced Artificial Venous Valve: Experimental Use in Pigs," Uflacker et al., Abstract No. 54C, 79$^{th}$ Scientific Assembly and Annual Meeting RSNA.

* cited by examiner

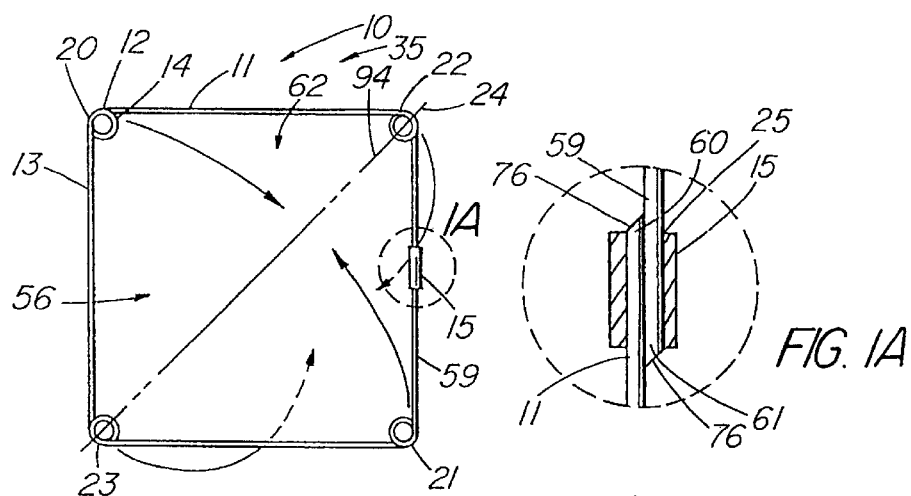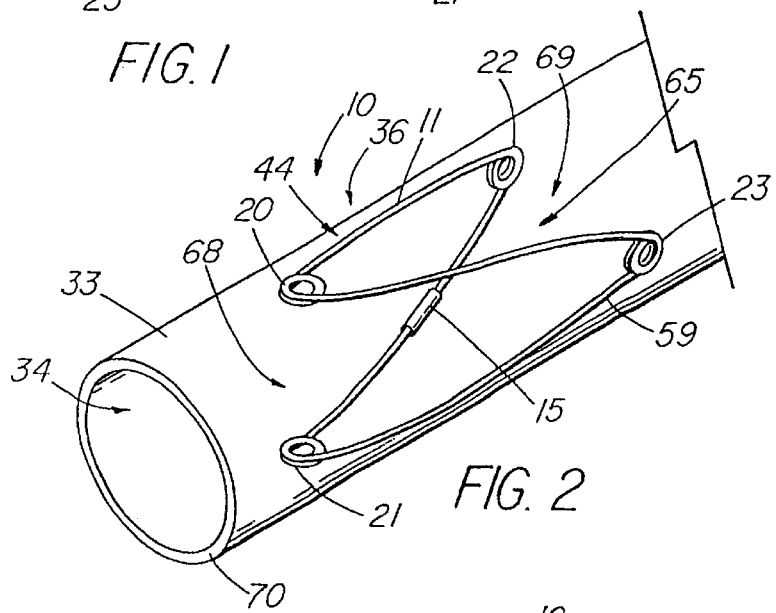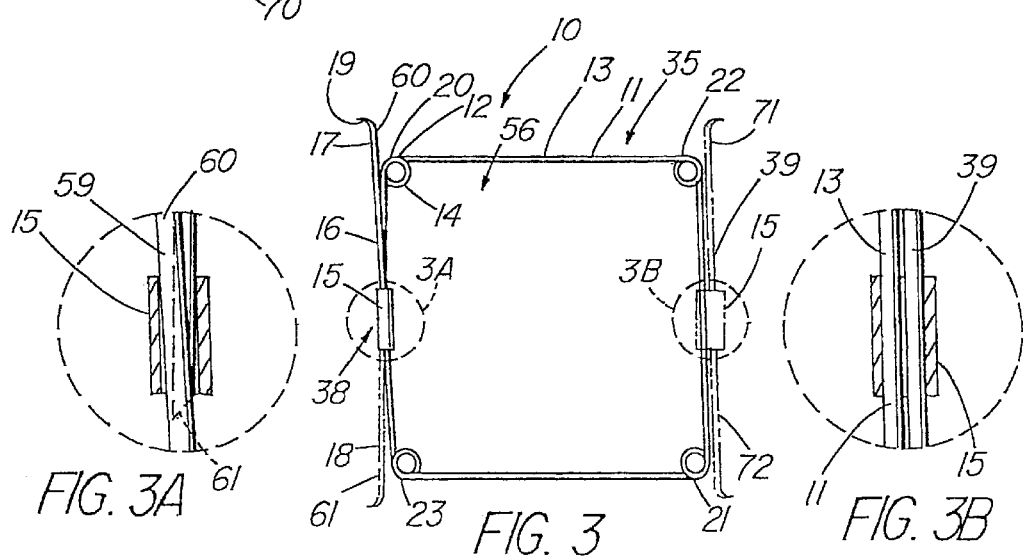

MULTIPLE-SIDED INTRALUMINAL MEDICAL DEVICE

CROSS-REFERENCE TO RELATED APPLICATIONS

This is a Continuation application of U.S. patent application Ser. No. 09/324,382 filed Jun. 2, 1999, now U.S. Pat. No. 6,200,336 B1, which claimed priority from U.S. Provisional patent application Serial No. 60/087,661 filed Jun. 28, 1998.

TECHNICAL FIELD

This invention relates to medical devices, more particularly, to intraluminal devices.

BACKGROUND OF THE INVENTION

As minimally invasive techniques and instruments for placement of intraluminal devices have developed over recent years, the number and types of treatment devices have proliferated as well. Stents, stent grafts, occlusion devices, artificial valves, shunts, etc., have provided successful treatment for a number of conditions that heretofore required surgery or lacked an adequate solution altogether. Minimally invasive intravascular devices have especially become popular with the introduction of coronary stents to the U.S. market in the early 1990s. Coronary and peripheral stents have been proven to provide a superior means of maintaining vessel patency, however, they have subsequently been used in conjunction with grafts as a repair for abdominal aortic aneurysm, fibers or other materials as occlusion devices, and as an intraluminal support for artificial valves, among other uses.

Some of the chief goals in designing stents and related devices include providing sufficient radial strength to supply sufficient force to the vessel and prevent device migration. An additional concern in peripheral use, is having a stent that is resistant to external compression. Self-expanding stents are superior in this regard to balloon expandable stents which are more popular for coronary use. The challenge is designing a device that can be delivered to the target vessel in as small of a configuration as possible, while still being capable of adequate expansion. Self-expanding stents usually require larger struts than balloon expandable stents, thus increasing their profile. When used with fabric or other coverings that require being folded into a delivery catheter, the problem is compounded.

There exists a need to have a basic stent, including a fabric covering, that is capable of being delivered with a low profile, while still having a sufficient expansion ratio to permit implantation in larger vessels, if desired, while being stable, self-centering, and capable of conforming to the shape of the vessel.

SUMMARY OF THE INVENTION

The foregoing problems are solved and a technical advance is achieved in an illustrative multiple-sided intraluminal medical device comprised of a single piece of wire or other material having a plurality of sides and bends interconnecting adjacent sides. The bends can be coils, fillets, or other configurations to reduce stress and fatigue. The single piece of wire is preferably joined by an attachment mechanism, such as a piece of cannula and solder, to form a closed circumference frame. The device has a first configuration wherein the sides and bends generally lie within a single, flat plane. In an embodiment having four equal sides, the frame is folded into a second configuration where opposite bends are brought in closer proximity to one another toward one end of the device, while the other opposite ends are folded in closer proximity together toward the opposite end of the device. In the second configuration, the device becomes a self-expanding stent. In a third configuration, the device is compressed into a delivery device, such as a catheter, such that the sides are generally beside one another. While the preferred embodiment is four-sided, other polygonal shapes can be used as well.

In another aspect of the present invention, one or more barbs can be attached to the frame for anchoring the device in the lumen of a vessel. The barbs can be extensions of the single piece of wire or other material comprising the frame, or they can represent a second piece of material that is separately attached to the frame by a separate attachment mechanism. An elongated barb can be used to connect additional devices with the second and subsequent frames attached to the barb in a similar manner.

In still another aspect of the present invention, a covering, such as DACRON, PTFE, collagen, or other flexible material, can be attached to the device with sutures or other means to partially, completely, or selectively restrict fluid flow. When the covering extends over the entire aperture of the frame, the frame formed into the second configuration functions as an vascular occlusion device that once deployed, is capable of almost immediately occluding an artery. A artificial valve, such as that used in the lower legs and feet to correct incompetent veins, can be made by covering half of the frame aperture with a triangular piece of material. The artificial vein traps retrograde blood flow and seals the lumen, while normal blood flow is permitted to travel through the device. In related embodiments, the device can be used to form a stent graft for repairing damaged or diseased vessels. In a first stent graft embodiment, a pair of covered frames or stent adaptors are used to secure a tubular graft prosthesis at either end and seal the vessel. Each stent adaptor has an opening through which the graft prosthesis is placed and an elongated barb is attached to both another stent graft embodiment, one or more frames in the second configuration are used inside a sleeve to secure the device to a vessel wall.

BRIEF DESCRIPTION OF THE DRAWING

FIG. 1 depicts a top view of one exemplary embodiment of the present invention;

FIG. 2 depicts a pictorial view of the embodiment of FIG. 1;

FIGS. 3 to 3B depict a top view and enlarged, partial cross-sectional views of a second exemplary embodiment of the present invention;

DETAILED DESCRIPTION

The invention is further illustrated by the following (preceding) pictorial embodiments, which in no way should be construed as further limiting. The present invention specifically contemplates other embodiments not illustrated but intended to included in the appended claims.

Figure 9:
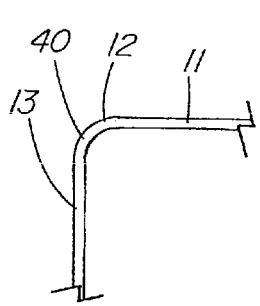
FIGS. 9–11 depict enlarged partial views of other embodiments of the present invention.
Figure 10:
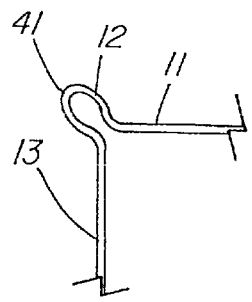
Figure 11:
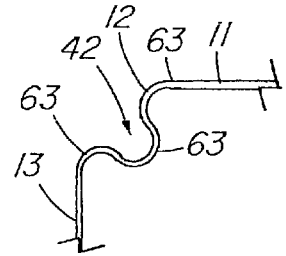
Figure 19:
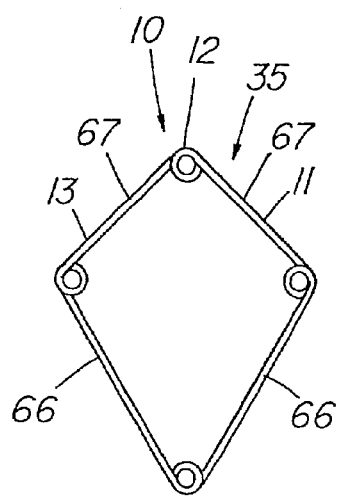
FIG. 19 depicts a top view of an eighth embodiment of the present invention.

FIG. 1 depicts a top view of one embodiment of the medical device 10 of the present invention comprising a frame 11 of resilient material, preferably metal wire made of stainless steel or a superelastic material (e.g., nitinol). While round wired is depicted in each of the embodiments shown herein, other types, e.g., flat, square, or triangular, may be used to form the frame. In the illustrative embodiment, the frame comprises a closed circumference 62 of a single piece 59 of material that is formed into a device 10 having a plurality of sides 13 interconnected by a series of bends 12. The depicted embodiment includes four sides 13 of approximately equal length. Alternative embodiment include forming a frame into any polygonal shape, for example a pentagon, hexagon, octagon, etc. One alternative embodiment is shown in FIG. 19 that includes a four-sided frame 11 having the general shape of a kite with two adjacent longer sides 66 and two adjacent shorter sides 67. In the embodiment of FIG. 1, the bends 12 interconnecting the sides 13 comprise a coil 14 of approximately one and a quarter turns. The coil bend produces superior bending fatigue characteristics than that of a simple bend 40, as shown in FIG. 9, when the frame is formed from stainless steel and most other standard materials. The embodiment of FIG. 9 may be more appropriate, however, if the frame is formed from nitinol (NiTi) or other superelastic alloys, as forming certain type of bends, such as coil 14, may actually decrease fatigue life of a device of superelastic materials. Therefore, the bend 12 should be of a structure that minimizes bending fatigue. Alternative bend 12 embodiments include a outward-projecting fillet 41 as shown in FIG. 10, and an inward-projecting fillet 42 comprising a series of curves 63, as shown in FIG. 11. Fillets are well known in the stent art as a means to reduce stresses in bends. By having the fillet extend inward as depicted in FIG. 11, there is less potential trauma to the vessel wall.

When using stainless steel wire, the size of the wire depends on the size of device and the application. An occlusion device, for example, preferably uses 0.010" wire for a 10 mm square frame, while 0.014" and 0.016" wire would be used for 20 mm and 30 mm frames, respectively. Wire that is too stiff can damage the vessel, not conform well to the vessel wall, and increase the profile of the device.

Returning to FIG. 1, the single piece 59 of material comprising the frame 11 is formed into the closed circumference by securing the first and second ends 60,61 with an attachment mechanism 15 such as a piece of metal cannula. The ends 60,61 of the single piece 59 are then inserted into the cannula 15 and secured with solder 25, a weld, adhesive, or crimping to form the closed frame 11. The ends 60,61 of the single piece 59 can be joined directly without addition of a cannula 15, such as by soldering, welding, or other methods to join ends 61 and 62. Besides, joining the wire, the frame could be fabricated as a single piece of material 59, by stamping or cutting the frame 11 from another sheet (e.g., with a laser), fabricating from a mold, or some similar method of producing a unitary frame.

The device 10 depicted in FIG. 1 is shown in its first configuration 35 whereby all four interconnections or bends 20,21,22,23 and each of the sides 13 generally lie within a single flat plane. To resiliently reshape the device 10 into a second configuration 36, shown in FIG. 2, the frame 11 of FIG. 1 is folded twice, first along a diagonal axis 24 with opposite bends 20 and 21 being brought into closer proximity, followed by opposite bends 22 and 23 being folded together and brought into closer proximity in the opposite direction. The second configuration 36, depicted in FIG. 2, has two opposite bends 20,21 oriented at the first end 68 of the device 10, while the other opposite bends 22,23 are oriented at the second end 69 of the device 10 and rotated approximately 180° with respect to bends 20 and 21 when viewed in cross-section. The medical device in the second configuration 36 can be used as a stent 44 to maintain an open lumen 34 in a vessel 33, such as a vein, artery, or duct. The bending stresses introduced to the frame 11 by the first and second folds required to form the device 10 into the second configuration 36, apply radial force against the vessel wall 70 to hold the device 10 in place and prevent vessel closure. Absent any significant plastic deformation occurring during folding and deployment, the device in the second configuration 36 when removed from the vessel or other constraining means, will at least partially return to the first configuration 35. It is possible to plastically form the device 10 into the second configuration 36, such that it does not unfold when restraint is removed. This might be particularly desired if the device is made from nitinol or a superelastic alloy.

Figure 6:
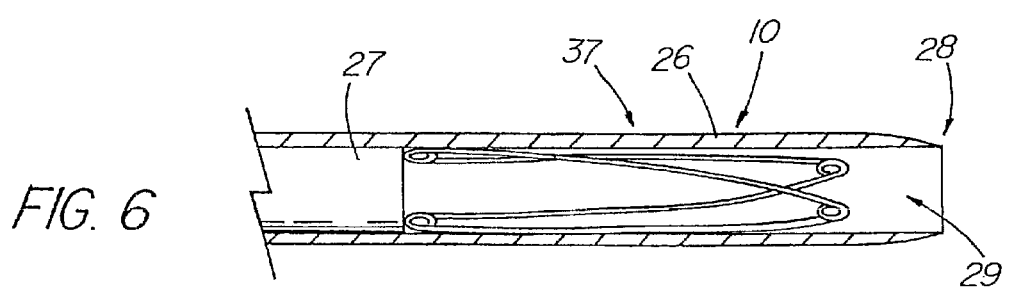
FIG. 6 depicts a partially-sectioned side view of the embodiment of FIG. 1 inside a delivery system.

The standard method of deploying the medical device 10 in a vessel 33, depicted in FIG. 6, involves resiliently forming the frame 11 into a third configuration 37 to load into a delivery device 26, such as a catheter. In the third configuration 37 the adjacent sides 13 are generally beside each other in close proximity. To advance and deploy the device from the distal end 28 of the delivery catheter 26, a pusher 27 is placed into the catheter lumen 29, When the device 10 is fully deployed, it assumes the second configuration 36 within the vessel as depicted in FIG. 2. The sides 13 of the frame, being made of resilient material, conform to the shape of the vessel wall 70 such that when viewed on end, the device 10 has a circular appearance when deployed in a round vessel.

A second embodiment of the present invention is depicted in FIG. 3 wherein one or more barbs 19 are included to anchor the device 10 following deployment. As understood, a barb can be a wire, hook, or any structure attached to the frame and so configured as to be able to anchor the device 10 within a lumen. The illustrative embodiment includes a first strut 17 with up to three other barbed struts 18,71,72, indicated in dashed lines, representing alternative embodiments. As depicted in detail view FIG. 3A, in the combination 38 that comprises struts 17 and 18, each strut is an extension of the single piece 59 of material of the frame 11 beyond the closed circumference 59. The attachment cannula 15 secures and closes the single piece 59 of material into the frame 11 as previously described, while the first and second ends 60,61 thereof, extend from the cannula 15, running generally parallel with the side 13 of the frame 11 from which they extend, each preferably terminating around or slightly beyond respective interconnections or bends 20,23. To facilitate anchoring, the distal end of the strut 17 in the illustrative embodiment contains a bend or hook defining barb 19.

Figure 4:
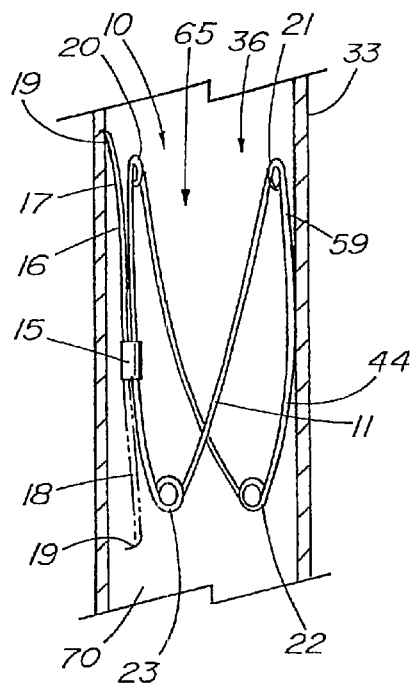
FIG. 4 depicts a side view of the embodiment of FIG. 3 deployed in a vessel.
Figure 5:
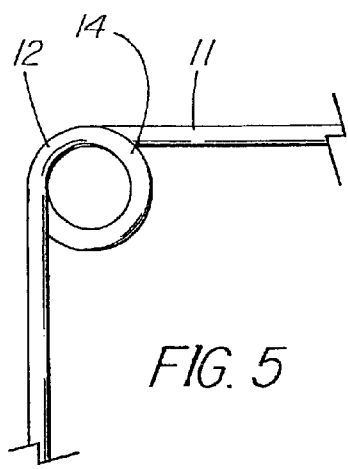
FIG. 5 depicts a enlarged partial view of the embodiment of FIG. 1.

Optionally, the tip of the distal end can be ground to a sharpened point for better tissue penetration. To add a third and fourth barb as shown, a double-barbed strut 39 comprising barbs 71 and 72 is attached to the opposite side 13 as defined by bends 21 and 22. Unlike combination 38, the double-barbed strut 39, as shown in detail view FIG. 3B, comprises a piece of wire, usually the length of combination 38, that is separate from the single piece 59 comprising the main frame 11. It is secured to the frame by attachment mechanism 15 using the methods described for FIG. 1. FIG. 4 depicts barb 19 of strut 17 engaging the vessel wall 70 while the device 10 is in the second, deployed configuration 36. While this embodiment describes up to a four barb system, more than four can be used.

Figure 7:
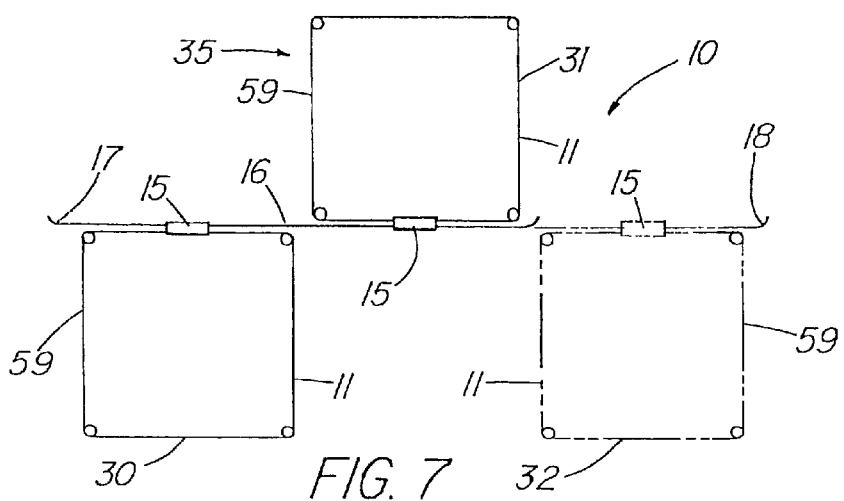
FIG. 7 depicts a top view of a third embodiment of the present invention.
Figure 8:
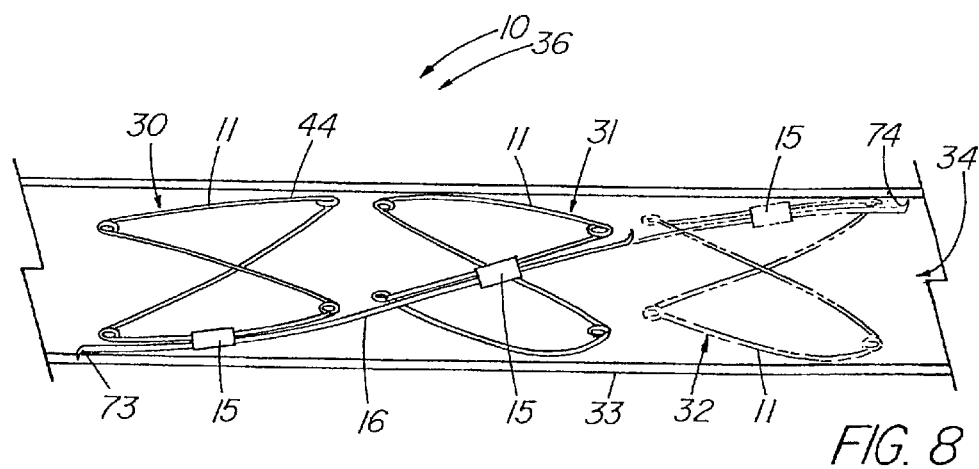
FIG. 8 depicts a side view of the embodiment of FIG. 7 deployed in a vessel.

FIG. 7 depicts a top view of a third embodiment of the present invention in the first configuration 35 that includes a plurality of frames 11 attached in series. In the illustrative embodiment, a first frame 30 and second frame 31 are attached by a strut 16 that is secured to each frame by their respective attachment mechanisms 15. The strut 16 can be a double-barbed strut 39 as shown in FIG. 3 (and detail view FIG. 3B) that is separate from the single pieces 59 comprising frames 30 and 31, or the strut may represent a long extended end of the one of the single pieces 59 as shown in detail view FIG. 3A. Further frames, such as third frame 32 shown in dashed lines, can be added by merely extending the length of the strut 16. FIG. 8 depicts a side view of the embodiment of FIG. 7 in the second configuration 36 as deployed in a vessel 33.

Figure 12:
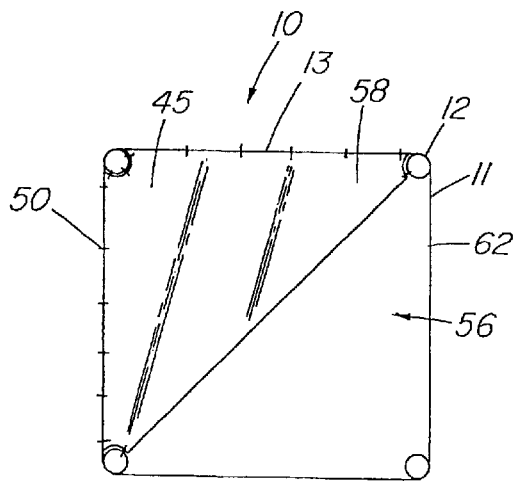
FIG. 12 depicts a top view of a fourth embodiment of the present invention.
Figure 13:
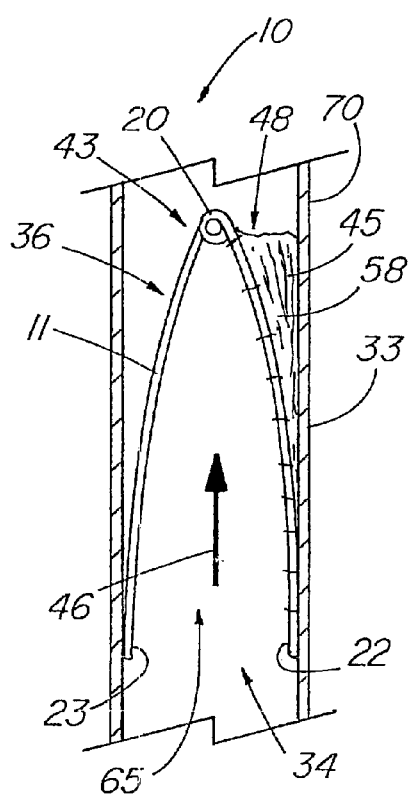
FIGS. 13–14 depicts side views of the embodiment of FIG. 12.
Figure 14:
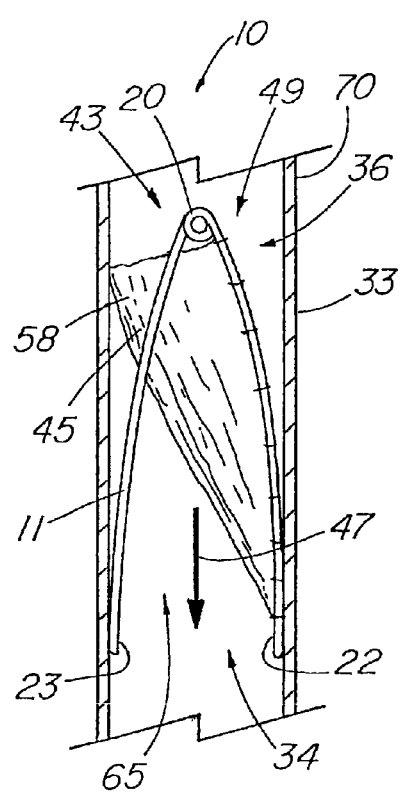

FIGS. 12–18 depict embodiments of the present invention in which a covering 45 comprising a sheet of fabric, collagen (such as small intestinal submucosa), or other flexible material is attached to the frame 11 by means of sutures 50, adhesive, heat sealing, "weaving" together, crosslinking, or other known means. FIG. 12 depicts a top view of a fourth embodiment of the present invention while in the first configuration 35, in which the covering 45 is a partial covering 58, triangular in shape, that extends over approximately half of the aperture 56 of the frame 11. When formed into the second configuration 36 as shown in FIGS. 13–14, the device 10 can act as an artificial valve 43 such as the type used to correct valvular incompetence. FIG. 13 depicts the valve 43 in the open configuration 48. In this state, the partial covering 58 has been displaced toward the vessel wall 70 due to positive fluid pressure, e.g., normal venous blood flow 46, thereby opening a passageway 65 through the frame 11 and the lumen 34 of the vessel 33. As the muscles relax, producing retrograde blood flow 47, as shown in FIG. 14, the partial covering 58 acts as a normal valve by catching the backward flowing blood and closing the lumen 34 of the vessel. In the case of the artificial valve 43, the partial covering 58 is forced against the vessel wall to seal off the passageway 65, unlike a normal venous valve which has two leaflets, which are forced together during retrograde flow. Both the artificial valve 43 of the illustrative embodiment and the normal venous valve, have a curved structure that facilitates the capture of the blood and subsequent closure. In addition to the triangular covering, other possible configurations of the partial covering 58 that result in the cupping or trapping fluid in one direction can be used.

Selecting the correct size of valve for the vessel ensures that the partial covering 58 properly seals against the vessel wall 70. If the lumen 34 of the vessel is too large for the device 10, there will be retrograde leakage around the partial covering 58.

Figure 15:
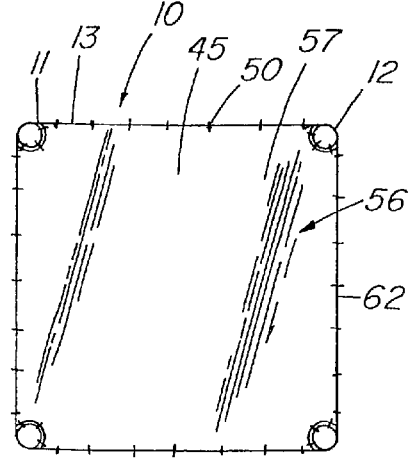
FIG. 15 depicts a top view of a fifth embodiment of the present invention.
Figure 16:
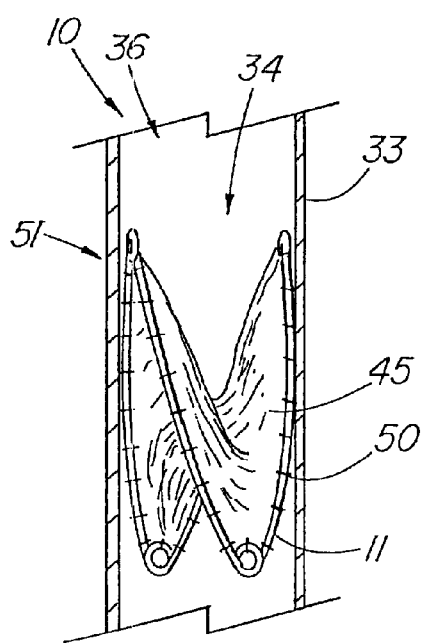
FIG. 16 depicts a side view of the embodiment of FIG. 15.

FIG. 15 depicts a top view of a fifth embodiment of the present invention in the first configuration 35, whereby there is a full covering 57 that generally covers the entire aperture 56 of the frame 11. When the device 10 is formed into the second configuration 36, as depicted in FIG. 16, it becomes useful as an occlusion device 51 to occlude a duct or vessel, close a shunt, repair a defect, or other application where complete prevention of flow is desired. As an intravascular device, studies in swine have shown occlusion to occur almost immediately when deployed in an artery or the aorta with autopsy specimens showed thrombus and fibrin had filled the space around the device. The design of the present invention permits it to be used successfully in large vessels such as the aorta. Generally, the occlusion device should have side 13 lengths that are at least around 50% or larger than the vessel diameter in which they are to be implanted.

Figure 17:
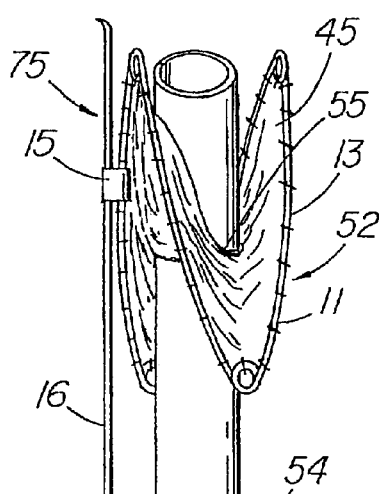
FIG. 17 depicts a side view of a sixth embodiment of the present invention.
Figure 18:
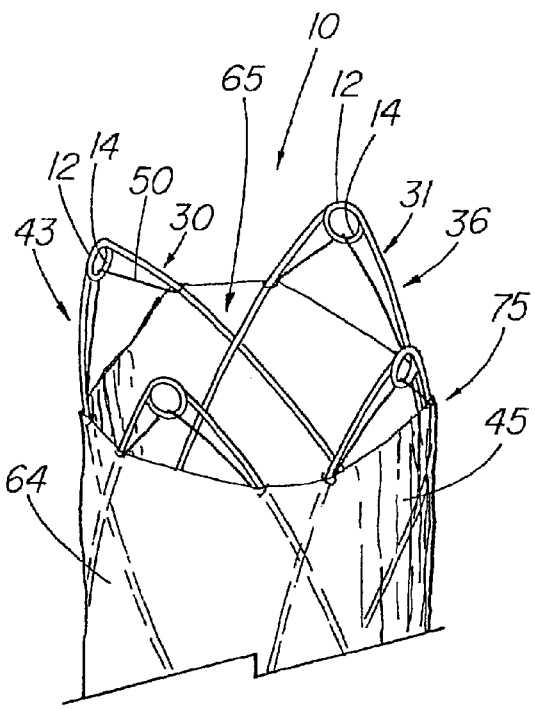
FIG. 18 depicts an enlarged pictorial view of a seventh embodiment of the present invention.

FIGS. 17–18 depict two embodiments of the present invention in which the device 10 functions as a stent graft 75 to repair a damaged or diseased vessel, such as due to formation of an aneurysm. FIG. 17 shown a stent graft 75 having a tubular graft prosthesis 54 that is held in place by a pair of frames 11 that function as stent adaptors 52,53. Each stent adaptor 52,53 has a covering attached to each of the frame sides 13 which includes a central opening 55 through which the graft prosthesis 54 is placed and held in place from friction or attachment to prevent migration. One method of preventing migration is placement of a smaller device of the present invention at each end and suturing it to the covering. The stent adaptors 52,53 provide a means to seal blood flow while centering the graft prosthesis in the vessel. A long double-ended strut 39 connects of each stent adaptor 52,53 and includes barb assists to further anchor the stent graft 75. In the embodiment depicted in FIG. 18, the covering 45 comprises an outer sleeve 64 that is held in place by first and second frames 30,31 that function as stents 44 to hold and seal the sleeve 64 against a vessel wall and maintain an open passageway 65. In the illustrative embodiment, the stents 44 are secured to the graft sleeve 64 by sutures 50 that are optionally anchored to the coils 14 of the bends 12. If the embodiment of FIG. 18 is used in smaller vessels, a single frame 11 can be used at each end of the stent graft 75.

What is claimed is:

1. A multiple-sided intraluminal medical device comprising:
    a first end and a second end;
    a frame having a first and a second configuration and closed circumference with an aperture therethrough, said closed circumference having a plurality of sides and a plurality of bends interconnecting said plurality of sides, said plurality of bonds in said first configuration comprising at least a first pair of opposite bends and a second pair of opposite bends;
    wherein said frame in said second configuration is folded on at least a diagonal axis across said aperture of said frame, bringing said first pair of opposite bends in closer proximity at said first end of said device and said second pair of opposite bends in closer proximity at second end of said device.

2. The device of claim 1, further including a covering attached to said plurality of sides.

3. The device of claim 2, wherein said covering includes an opening therethrough.

4. The device of claim 2, wherein said covering is attached to at least two of said plurality of sides.

5. The device of claim 4, wherein said covering is attached to each of said plurality sides.

6. The device of claim 5, wherein said covering includes an opening therethrough.

7. The device of claim 1, wherein said frame includes four sides and four interconnecting bends.

8. The device of claim 1, wherein at least said first pair of opposite bends are disposed on a diagonal axis across said aperture of said frame.

9. The device of claim 1, wherein said device with said frame in said second configuration includes a generally circular appearance when viewed from at least one of said first and said second ends.

10. A multiple-sided intraluminal medical device comprising:
   a first end and a second end;
   a frame having a first and a second configuration and closed circumference with an aperture therethrough, said closed circumference having a plurality of sides and a plurality of bends interconnecting said plurality of sides, said plurality of bends in said first configuration comprising at least a first pair of non-adjacent bends and a second pair of non-adjacent bends;
   wherein said frame in said second configuration is folded on at least a diagonal axis across said aperture of said frame, bringing said first pair of non-adjacent bends in closer proximity at said first end of said device and said second pair of non-adjacent bends in closer proximity at second end of said device.

11. The device of claim 10, further including a covering attached to said plurality of sides.

12. The device of claim 11, wherein said covering includes an opening therethrough.

13. The device of claim 10, wherein a covering is attached to at least two of said plurality of sides.

14. The device of claim 10, wherein a covering is attached to each of said plurality sides.

15. The device of claim 14, wherein said covering includes an opening therethough.

16. The device of claim 10, wherein said frame includes four sides and four interconnecting bends.

17. The device of claim 10, wherein said device with said frame in said second configuration includes a generally circular appearance when viewed from at least one of said first and said second ends.

18. A multiple-sided intraluminal medical device comprising:
   a frame being of a generally polygonal shape with a closed circumference and an aperture therethrough, said closed circumference having a plurality of sides and a series of interconnecting bends, and
   a covering attached to said frame and extending across the aperture thereof;
   wherein said frame is resiliently foldable across a diagonal axis of said aperture of said frame into a self-expanding stent configuration in which the covering forms a curved configuration adapted to trap fluid flowing in a single direction within a vessel.

19. The device of claim 18 wherein said covering is adapted to restrict fluid flow within the aperture of the frame.

20. The device of claim 18 wherein said covering includes an opening therethrough.

21. The device of claim 18 wherein said covering comprises small intestinal submucosa.

* * * * *